(12) United States Patent
Hohlbein

(10) Patent No.: US 7,182,542 B2
(45) Date of Patent: Feb. 27, 2007

(54) DISPOSABLE TOOTHBRUSH

(75) Inventor: Douglas Hohlbein, Pennington, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 11/072,931

(22) Filed: Mar. 4, 2005

(65) Prior Publication Data

US 2005/0147458 A1    Jul. 7, 2005

Related U.S. Application Data

(63) Continuation of application No. PCT/US2003/027455, filed on Sep. 4, 2003.

(60) Provisional application No. 60/408,321, filed on Sep. 5, 2002.

(51) Int. Cl.
A45B 11/00 (2006.01)
(52) U.S. Cl. ........................ 401/268; 401/132
(58) Field of Classification Search ................ 401/282, 401/284, 286, 118, 119, 132, 133
See application file for complete search history.

(56) References Cited

U.S. PATENT DOCUMENTS

| | | |
|---|---|---|
| 792,471 A | 6/1905 | Smith |
| 846,900 A | 3/1907 | Bloom |
| 876,185 A | 1/1908 | Hillman |
| 1,214,556 A | 2/1917 | Vene et al. |
| 1,411,681 A | 4/1922 | Burlew |
| 1,500,722 A | 7/1924 | Roush |
| 1,575,317 A | 3/1926 | Carmichael |
| 1,602,531 A | 10/1926 | Itoh |
| 1,784,986 A | 12/1930 | Eisenberg |
| 1,796,367 A | 3/1931 | Grove |
| 1,811,833 A | 6/1931 | Simon |
| RE19,006 E | 11/1933 | Graves |
| 1,950,767 A | 3/1934 | Abbott |
| 1,968,303 A | 7/1934 | McMath |
| 1,995,374 A * | 3/1935 | Young ..................... 401/268 |
| 2,077,758 A | 4/1937 | Johnson et al. |
| 2,233,831 A | 3/1941 | Burke |
| 2,241,584 A | 5/1941 | Cohen |
| 2,262,982 A | 11/1941 | Wolcott |
| 2,307,493 A * | 1/1943 | Davidson ................. 401/268 |
| 2,386,085 A | 10/1945 | Babel |
| 2,649,959 A | 8/1953 | Hallahan |

(Continued)

FOREIGN PATENT DOCUMENTS

CH    664 271 A5    2/1988

(Continued)

*Primary Examiner*—Huyen Le
(74) *Attorney, Agent, or Firm*—Ellen K. Park

(57) ABSTRACT

A waterless, disposable toothbrush is disclosed and includes a handle having a toothpick connected thereto to enable cleaning between teeth, and a rupturable dispenser containing a dentifrice and being connected in a bristle portion of the toothbrush head for dispensing the dentifrice to the teeth to provide teeth cleaning and breath freshening, all of which deliver a cleaning, polishing, whitening, between teeth cleaning, and breath freshening action. The disposable toothbrush of the present invention combines three benefits into one disposable toothbrush: (1) tooth surface cleaning with the toothbrush bristles and the dentifrice in the rupturable dispenser; (2) between teeth cleaning with the toothpick; and (3) breath freshening with the dentifrice in the rupturable dispenser.

6 Claims, 1 Drawing Sheet

U.S. PATENT DOCUMENTS

| | | |
|---|---|---|
| 2,710,982 A | 6/1955 | Gillem |
| 2,736,917 A * | 3/1956 | Goldstein et al. ......... 15/104.94 |
| 2,778,045 A | 1/1957 | Bly et al. |
| 3,068,571 A | 12/1962 | Thompson |
| 3,078,856 A | 2/1963 | Bender et al. |
| 3,103,935 A | 9/1963 | Woodrow |
| 3,165,776 A | 1/1965 | Tuseth |
| 3,458,268 A * | 7/1969 | Wozab et al. ................ 401/261 |
| 3,491,396 A * | 1/1970 | Granieri, Jr. et al. .... 15/104.94 |
| 3,536,410 A * | 10/1970 | Wargoe ....................... 401/132 |
| 3,609,789 A | 10/1971 | Slater |
| 3,698,405 A | 10/1972 | Walker |
| 3,917,420 A | 11/1975 | Watson |
| 4,194,290 A | 3/1980 | Vallhonrat |
| 4,292,304 A | 9/1981 | Barels et al. |
| D278,863 S | 5/1985 | Bradley |
| 4,864,676 A | 9/1989 | Schaiper |
| 4,911,187 A | 3/1990 | Castillo |
| 5,052,071 A * | 10/1991 | Halm ......................... 15/167.1 |
| 5,061,106 A * | 10/1991 | Kent ........................... 401/268 |
| 5,133,971 A | 7/1992 | Copelan et al. |
| 5,390,984 A | 2/1995 | Boucherie et al. |
| 5,393,796 A | 2/1995 | Halberstadt et al. |
| 5,533,791 A | 7/1996 | Boucherie |
| 5,609,890 A | 3/1997 | Boucherie |
| D378,711 S | 4/1997 | Occhetti |
| 5,860,183 A | 1/1999 | Kam |
| 5,888,002 A | 3/1999 | Fenstersheib |
| 6,004,059 A | 12/1999 | Zaccaria |
| 6,135,274 A | 10/2000 | James |
| 6,321,407 B1 | 11/2001 | Weihrauch |
| 6,397,860 B1 | 6/2002 | Hill |
| 6,524,023 B2 | 2/2003 | Andersen |
| 6,526,993 B1 | 3/2003 | Wagner |
| 6,602,013 B2 * | 8/2003 | Clark .......................... 401/282 |
| 2002/0175101 A1 | 11/2002 | Albert |
| 2003/0188761 A1 | 10/2003 | Garcia et al. |

FOREIGN PATENT DOCUMENTS

| | | |
|---|---|---|
| DE | 3529953 | 3/1987 |
| DE | 4127429 | 2/1993 |
| DE | 42 31 817 A1 | 3/1994 |
| DE | 19531368 | 2/1997 |
| DE | 19842984 | 8/2000 |
| EP | 0 475 314 A1 | 3/1992 |
| EP | 0 481 926 B1 | 4/1992 |
| EP | 0 872 195 | 10/1998 |
| FR | 2 646 068 A | 10/1990 |
| FR | 2 654 598 A | 5/1991 |
| FR | 2 754 436 A | 4/1998 |
| FR | 2 772 569 A | 6/1999 |
| FR | 2 822 658 | 10/2002 |
| FR | 2 822 658 A1 | 10/2002 |
| GB | 228460 | 2/1925 |
| GB | 746649 | 3/1956 |
| GB | 2351015 | 12/2000 |
| GB | 2388529 | 11/2003 |
| GB | 2 394 653 A | 5/2004 |
| JP | 10-216158 | 8/1998 |
| JP | 2003 245133 A | 9/2003 |
| WO | WO 99/60886 | 12/1999 |
| WO | WO 02/34083 A1 | 5/2002 |
| WO | WO 02/058508 A2 | 8/2002 |
| WO | WO 03/037210 A1 | 5/2003 |
| WO | WO 2004/021914 A2 | 3/2004 |
| WO | WO 2004/010821 A1 | 5/2004 |

* cited by examiner

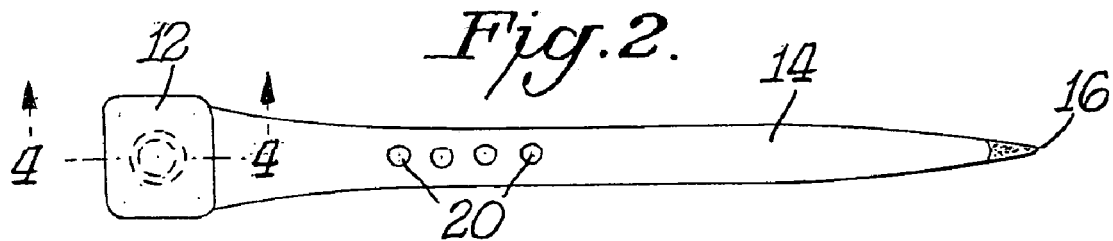
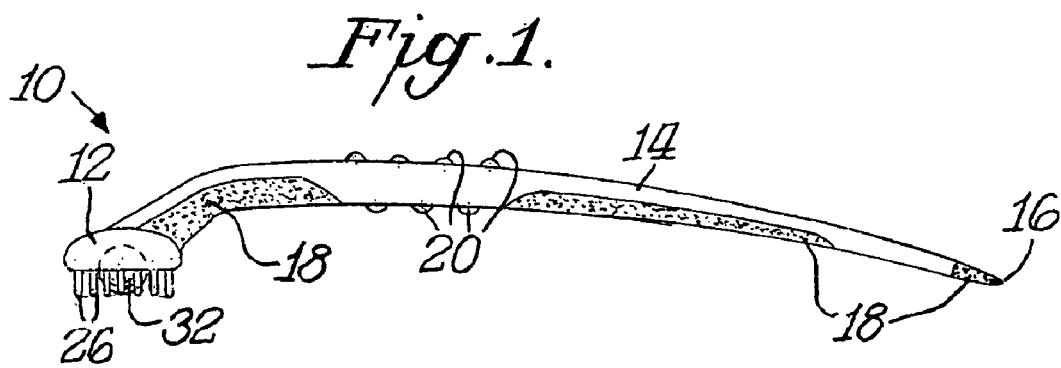
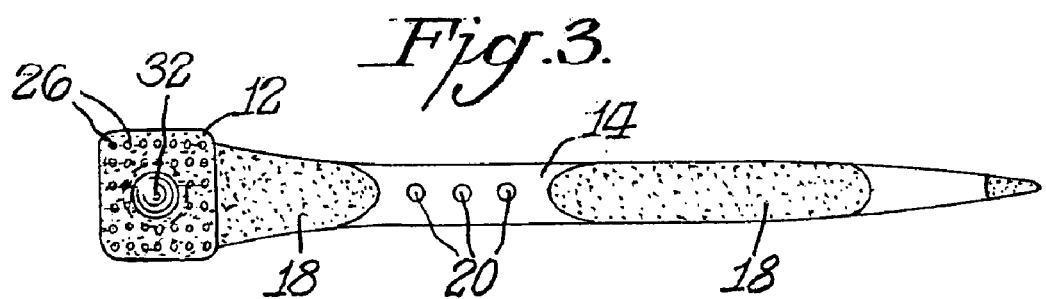
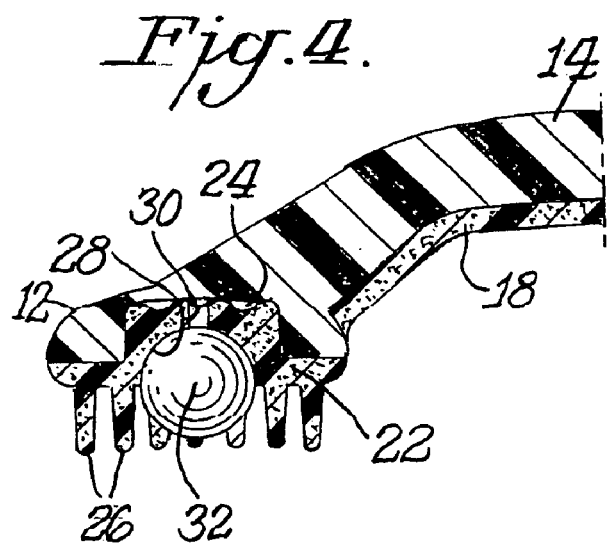

DISPOSABLE TOOTHBRUSH

This is a continuation of International Application PCT/US2003/027455 filed Sep. 4, 2003, which claims the benefit of Provisional Application Ser. No. 60/408,321, filed Sep. 5, 2002, both of which are incorporated by reference herein in their entirety.

BACKGROUND OF THE INVENTION

A. Field of the Invention

The present invention relates generally to toothbrushes, and, more particularly, to a disposable toothbrush having a breath freshening, teeth cleaning gel capsule, and a toothpick.

B. Description of the Related Art

The advantages of good dental hygiene are well known. Often, however, toothbrushes are forgotten when one is traveling or away from home. Hotels, health care facilities, nursing homes, hospitals, daycare facilities, schools, airlines, etc. have a need for single use disposable toothbrushes that may be economically supplied to and discarded by individuals without a toothbrush and/or a water supply. Such toothbrushes could be used in vending machines, or distributed in large quantities for simple, portable use from anywhere.

Various types of disposable toothbrushes are known in the art. For example, some toothbrush systems have attempted to meet some of these needs by providing toothpaste within the toothbrush itself, through an integrated channel, for distribution through the toothbrush and around the bristles. This approach can be less economical due to the added manufacturing costs of toothbrushes with integrated channels. In addition, the toothpaste in some of these integrated channel toothbrushes, not being properly sealed, has a tendency to become dry, hard and stale.

U.S. Pat. No. 6,135,274 shows an apparatus for brushing teeth that includes an outer bag, a toothbrush sealed within the outer bag, and a dispenser sealed within the outer bag and containing a mouth care solution. In use, the rupturable dispenser is squeezed or otherwise subjected to pressure while the toothbrush remains sealed within the outer bag. Unfortunately, the apparatus for brushing teeth requires an outer bag, increasing the cost of the apparatus, and fails to provide the rupturable dispenser and toothbrush as one complete, connected unit. The reference also fails to provide a toothpick mechanism for cleaning in between teeth, and which is also connected to the toothbrush.

U.S. Pat. No. 6,397,860 discloses a disposable, waterless tooth brushing assembly that includes a toothbrush, a non-foaming, saliva-activated, teeth-cleaning agent pre-applied to the bristles of the toothbrush, a small moistened disposable towel for user after teeth cleaning, and a compact, lightweight, two-layer heat-sealed packaging container for pre-use sanitary storage of the toothbrush and towel. Like U.S. Pat. No. 6,135,274, the assembly of U.S. Pat. No. 6,397,860 requires a packaging container, increasing the cost of the assembly, and fails to provide a rupturable dispenser and toothbrush as one complete, connected unit. The reference also fails to provide a toothpick mechanism for cleaning in between teeth, and which is also connected to the toothbrush.

None of the toothbrush assemblies of the related art includes a rupturable dispenser containing a dentifrice, a toothpick, and a toothbrush as one complete, connected unit. Thus, there is a need in the art for a waterless, disposable toothbrush having a toothpick connected thereto to enable cleaning in between teeth, and a rupturable dispenser containing a dentifrice and being connected in the bristle portion of the toothbrush for dispensing the dentifrice to the teeth to provide teeth cleaning and breath freshening.

SUMMARY OF THE INVENTION

The present invention solves the problems of the related art by providing a waterless, disposable toothbrush having a toothpick connected thereto to enable cleaning in between teeth, and a rupturable dispenser containing a dentifrice and being connected in the bristle portion of the toothbrush for dispensing the dentifrice to the teeth to provide teeth cleaning and breath freshening, all of which deliver a cleaning, polishing, whitening, between teeth cleaning, and breath freshening action in addition to enhancing the cleaning efficiency of a typical disposable toothbrush. The disposable toothbrush of the present invention combines three benefits into one disposable toothbrush: (1) tooth surface cleaning provided by the toothbrush bristles and the dentifrice in the rupturable dispenser; (2) between teeth cleaning provided by the toothpick; and (3) breath freshening provided by the dentifrice in the rupturable dispenser.

As embodied and broadly described herein, the present invention is broadly drawn to a disposable toothbrush, preferably comprising: a handle having a toothpick formed at one end thereof; and a head connected at another end of said handle, said head having a bristle block that includes a plurality of bristles and retains a gel capsule therein, the gel capsule containing a mouth care solution. In further embodiments, the gel capsule can be replaced by a quantity of toothpowder, toothpaste or a tooth cleaning gel dentifrice, to provide the cleaning benefits of the dentifrice within the rupturable dispenser.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. It is to be understood that both the foregoing general description and the following detailed description are exemplary and explanatory only and are not restrictive of the invention, as claimed.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 1 is a side elevational view of a disposable toothbrush with a toothpick and a breath freshening, teeth cleaning gel capsule connected thereto in accordance with an embodiment of the present invention;

FIG. 2 is a top plan view of the disposable toothbrush shown in FIG. 1;

FIG. 3 is a bottom plan view of the disposable toothbrush shown in FIGS. 1–2; and FIG. 4 is a fragmental, cross-sectional view of the disposable toothbrush shown in FIGS. 1–3, taken along line 4—4 of FIG. 2.

DETAILED DESCRIPTION OF EMBODIMENTS OF THE INVENTION

The following detailed description of the invention refers to the accompanying drawings. The same reference numbers in different drawings identify the same or similar elements. Also, the following detailed description does not limit the invention. Instead, the scope of the invention is defined by the appended claims and equivalents thereof.

FIGS. 1–4 illustrate one practice of the present invention wherein a disposable toothbrush 10 includes a head 12 and a handle 14. Head 12 may be a refill head and thus be removably connected to handle 14, or head 12 may be permanently connected to head 12 within the practice of the present invention.

The majority of handle 14 and a portion of head 12 may be molded from a variety of rigid materials, including plastics, resins, etc., such as, for example, polypropylene. An end portion of handle 14, opposite the end head 12 is attached to, preferably includes a toothpick 16 formed of a resilient and soft thermoplastic elastomer. Toothpick 16 may be a refill and thus be removably connected to handle 14, or toothpick 16 may be permanently connected to handle 14 within the practice of the present invention. Toothpick 16 provides a mechanism for spot cleaning between teeth. Forming toothpick 16 of a soft elastomer provides more comfortable interproximal cleaning between teeth.

Portions 18 of handle 14 may also be formed of a resilient and soft thermoplastic elastomer. The thermoplastic elastomer which forms toothpick 16 and handle portions 18 may be a thermoplastic vulcanate (TPV) consisting of a mixture of polypropylene and EPDM (ethylene propylene diene monomers) which is available as SANTOPRENE (brand), described in U.S. Pat. No. 5,393,796, or VYRAM (brand), another TPV consisting of a mixture of polypropylene and natural rubber. Both SANTOPRENE and VYRAM (brands) are elastomers marketed by Advanced Elastomer Systems. Other suitable elastomers include KRATON, a brand of styrene block copolymer (SBC) marketed by Shell, and DYNAFLEX G 2706 (brand), a thermoplastic elastomer marketed by GLS Corporation and which is made with KRATON (brand) polymer.

Handle 14 may further include dimples, bumps, or ridges 20 protruding from portions of its surface, and providing a decorative appearance to handle 14 and enhanced gripping of handle 14 during use of toothbrush 10. Dimples 20 may be formed from the same material as soft elastomer portions 18 of handle 14 or from the same material as the majority of handle 14 (e.g., a rigid material such as polypropylene).

Another portion of head 12, defining a bristle block 22 of head 12, may also be formed of a resilient and soft thermoplastic elastomer, such as the thermoplastic elastomer used to form toothpick 16 and handle portions 18. Bristle block 22 may include depressions 24 provided in a surface thereof that provide a cushioning effect to a reputurable dispenser, preferably a gel capsule 32, contained therein, as described more fully below. Bristle block 22 further includes a multitude of conventional filament, preferably nylon, or elastomeric bristles or fingers 26 extending outwardly from head 12. In the illustrated embodiment as best shown in FIG. 4, bristles 26 extend outwardly from the outer surface of bristle block 22 the same distance so as to create a generally flat surface. Alternatively, however, some bristles 26 may be shorter or longer than other bristles 26.

The term "bristles" as used herein is intended to be used in a generic sense as cleaning elements or massage elements arranged in a circular cross-section shape or any type of desired shape, including straight portions or sinusoidal portions. It is to be understood that the specific illustration of the bristles is merely for exemplary purposes. The invention can, however, be practiced with various combinations of the same or different bristle configurations (such as stapled, in-mold tufting (IMT) technology as disclosed in U.S. Pat. Nos. 5,609,890, 5,390,984, and 5,533,791, the disclosures of which being incorporated by reference herein in their entirety, etc.) and/or with the same or different bristle materials (such as nylon bristles, spiral bristles, rubber bristles, etc.). Similarly, while FIGS. 1–4 illustrate the bristles 26 to be generally perpendicular to the outer surface of head 12, some or all of the bristles 26 may be angled at various angles with respect to the outer surface of head 12. It is thereby possible to select the combination of bristle configurations, bristle materials and bristle orientations to achieve specific intended results, such as enhanced cleaning, tooth polishing, breath freshening, tooth whitening and/or massaging of the gums.

As stated above, the bristle block 22 may include one or more depressions 24 which are designed to receive and retain a rupturable dispenser, such as a gel capsule 32 therein. The one or more depressions 24 can be varied in size so as to accommodate not only varying size gel capsules 32, but varying quantities of toothpowder, a toothpaste or tooth cleaning gel dentifrice, for delivery to the denture as the bristles 26 extending from the bristle block 22 are applied thereto, during use of the present invention such that the toothpowder, toothpaste or tooth cleaning gel dentifrice enhance the cleaning of the denture by the bristles. While the present invention can be manufactured containing a packed toothpowder, toothpaste or tooth cleaning gel dentifrice and used repeatedly by the user refilling the dispenser with toothpowder, toothpaste paste or tooth cleaning gel dentifrice, it is preferably used with one or more gel capsules 32 contained therein. Most preferably the present invention is used with a single gel capsule 32, supplied therewith, so as to be most easily transported, used, and subsequently disposed of; however, it may also be used repeatedly with replaceable gel capsules 32, and then disposed of.

It is preferred that the depression is in the form of a cushioned socket 28 sized and shaped to receive and retain the gel capsule 32, without premature rupture of the gel capsule 32 prior to use thereof during application of the bristle block 22 to the denture and brushing thereof. Cushioning socket 28 opening 30, and the material making up bristle block 22 provide a cushioning effect for gel capsule 32 to prevent gel capsule 32 from rupturing prior to use.

Gel capsule 32 holds and applies a mouth care solution onto bristle 26 of toothbrush head 12. The mouth care solution may be a toothpaste, a gel, a mouthwash, or similar dentifrice or oral hygiene product, or a combination of the same. Preferably gel capsule 32 is a liquid-filled gel capsule having frangible, thin walls that easily rupture when rubbed against the teeth, or dissolve when mixed with the saliva of a user. The materials making up gel capsule 32 and the mouth care solution contained therein preferably are consumable by the user of toothbrush 10, eliminating the need for water, a sink, or a waste receptacle to expectorate the gel capsule 32 or its contents. The mouth care solution remains in gel capsule 32 until toothbrush 10 is ready for use. Preferably, gel capsule 32 is fully sealed, helping the mouth care solution to remain fresh until use.

In use, gel capsule 32 would be pressed against the teeth and rupture or dissolve, applying the mouth care solution over bristles 26. The user then may brush their teeth with toothbrush 10. The user may also use toothpick 16 to clean between teeth, either before or after brushing. After the user has used toothbrush 10, one may, but not necessarily, then easily and economically dispose of toothbrush 10.

In a preferred aspect of the present invention, the entire structure of toothbrush 10, including head 12, handle 14, and toothpick 16, is molded as one integral structure, using a conventional two-component injection molding operation typically used in the manufacture of toothbrushes. This enables toothbrush 10 to be economically and quickly manufactured. Although toothbrush 10 may have a variety of sizes and dimensions, it is preferred that toothbrush 10 have a small profile, with head 12 being small enough to cover one tooth at a time and handle being thinner than conventional, everyday toothbrush handles. As shown in FIGS. 3–4, the head is small enough such that the retaining socket further comprises an outer peripheral edge and a diameter, the head further comprises an outer peripheral edge, and wherein any radial distance between the outer peripheral edge of the uncovered retaining socket and the outer peripheral edge of the head is less than or approximately equal to the diameter of the retaining socket, and also preferably wherein any radial distance between the outer peripheral edge of the retaining socket and of the head is less than twice the diameter of the retaining socket.

The disposable toothbrush 10 of the present invention provides many benefits, including the cosmetic benefits of brushing one's teeth in a form that can be used when one is away from home, and away from a water supply. The cosmetic benefits achieved by the disposable toothbrush 10 of the present invention include the cleaning of debris between teeth with toothpick 16, broad tooth surface cleaning (particularly the front teeth) with bristles 26 and the mouth care solution of gel capsule 32, and breath freshening with the mouth care solution of gel capsule 32.

In addition to the cosmetic benefits, the disposable toothbrush 10 of the present invention also provides economic benefits in the form of an inexpensive toothbrush that is both quickly and economically manufactured. Disposable toothbrush 10 also provides a mechanism for maintaining oral health, without the need for toothpaste, water, mouth wash, and containers to hold the same. Thus, disposable toothbrush 10 is also very convenient to use.

It will be apparent to those skilled in the art that various modifications and variations can be made in the powered toothbrush of the present invention and in construction of the toothbrush without departing from the scope or spirit of the invention, examples of which have been previously provided.

Although FIGS. 1–4 illustrate a manually-operated, disposable toothbrush, the present invention may also be practiced where the head includes one or more power or electrically operated movable sections carrying cleaning elements. Such movable section may oscillate in a rotational manner or may oscillate linearly in a longitudinal direction with respect to the longitudinal axis of the head or may oscillate linearly in a lateral or transverse direction with respect to the longitudinal axis of the head. The movable section may oscillate in and out in a direction toward and away from the outer surface of the head. The movable section may rock back and forth with respect to the outer surface of the head. The movable section may rotate continuously in the same direction, rather than oscillate. Any suitable drive mechanism may be used for imparting the desired motion to the movable section. Where plural movable sections are used, all of the movable sections may have the same type and direction of movement, or combinations of different movements may be used.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A toothbrush, comprising:
    a handle;
    a head connected at one end of the handle, the head having an outer surface formed from a first material and a plurality of cleaning elements extending from the outer surface; and a retaining socket formed in the head and surrounded by the cleaning elements for retaining a capsule therein, the retaining socket formed from the first material and having sidewalls and a floor to prevent a capsule retained therein from passing through the head, wherein the retaining socket further comprises an outer peripheral edge and a diameter, the head farther comprises an outer peripheral edge, and wherein any radial distance between the outer peripheral edge of the retaining socket and the outer peripheral edge of the head is less than or approximately equal to the diameter of the retaining socket.

2. The toothbrush of claim 1, wherein any radial distance between the outer peripheral edge of the retaining socket and of the head is less than twice the diameter of the retaining socket.

3. A method of using of a toothbrush comprising,
    providing a toothbrush having a handle and a head connected at one end of said handle, said head comprising a plurality of cleaning elements surrounding a depression, which depression contains a dispenser containing a particulate-free mouth care material,
    applying the cleaning elements to the denture until the dispenser ruptures, such that the mouth care material is applied to the cleaning elements and the denture, wherein the dispenser is securely retained in the depression such that the dispenser is prevented from unintentional dislodgement prior to rupture, and
    consuming the dispenser and mouth care material,
    wherein the dispenser comprises a liquid breath freshener, and
    wherein the depression includes a cushioning socket for receiving and retaining the dispenser therein.

4. The method of claim 3, wherein the cushioning socket includes a further opening provided between said dispenser and the head to prevent trapping air in the cushioning socket when the dispenser is inserted in the cushioning socket and to prevent the dispenser from rupturing prior to application of the dispenser to the denture.

5. The method of claim 3, wherein the dispenser is a spherical, liquid-filled gel capsule having frangible, thin walls that rupture when rubbed against the teeth or dissolve when mixed with saliva.

6. The method of claim 3, wherein the dispenser is not retained by the cleaning elements prior to rupture.

* * * * *